Figure 1:
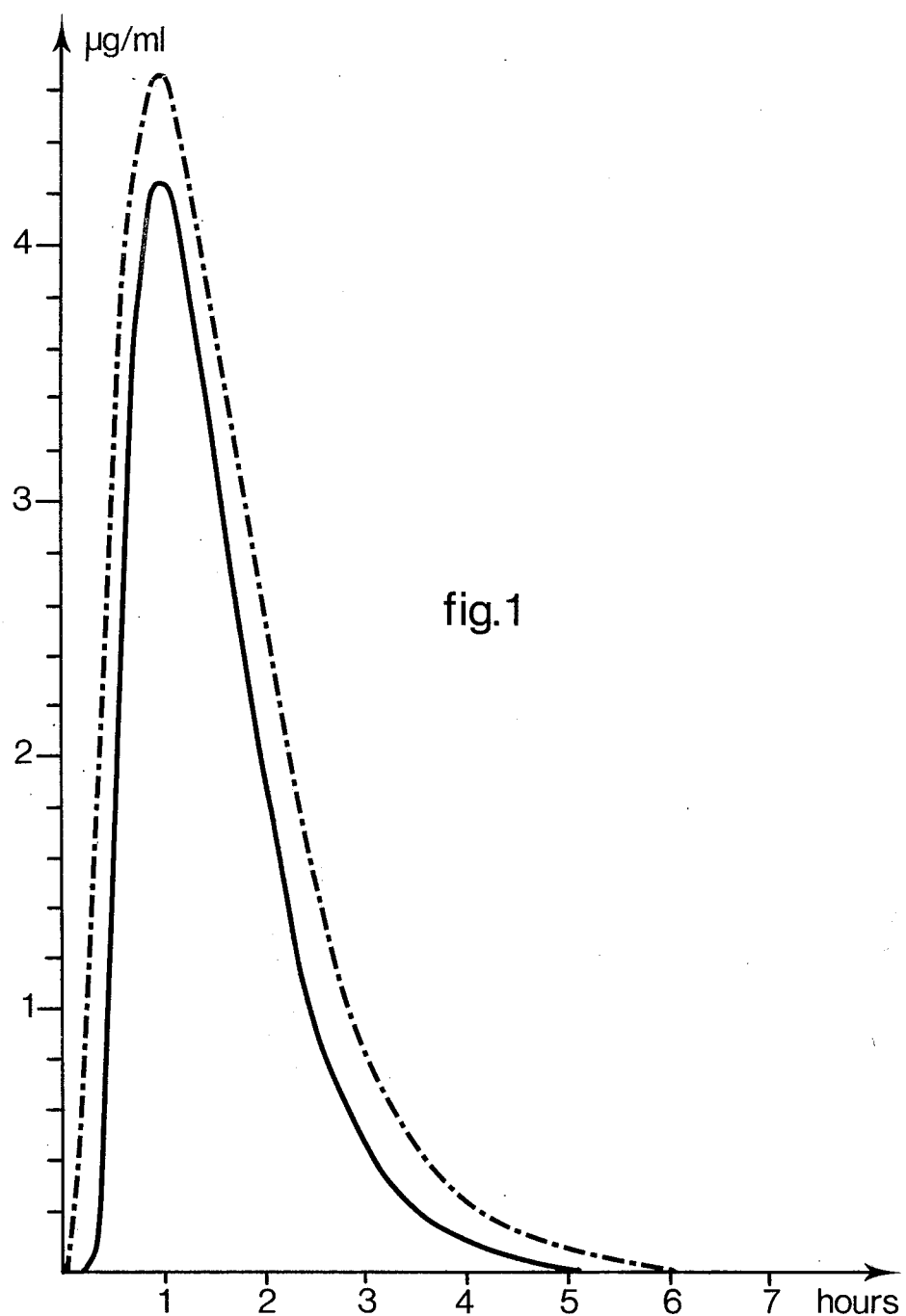

United States Patent [19]

Godtfredsen et al.

[11] 4,325,960
[45] Apr. 20, 1982

[54] 6-AMIDINOPENICILLANIC ACID DERIVATIVES INCLUDING THE RADICAL OF A β-LACTAMASE INHIBITOR

[75] Inventors: Wagn O. Godtfredsen, Vaerlose; Welf von Daehne, Rungsted Kyst, both of Denmark

[73] Assignee: Leo Pharmaceutical Products Ltd. A/S (Lovens Kemiske Fabrik Produktionsaktieselskab), Ballerup, Denmark

[21] Appl. No.: 116,651

[22] Filed: Jan. 29, 1980

[30] Foreign Application Priority Data

Feb. 13, 1979 [GB] United Kingdom ............... 05021/79
Jun. 19, 1979 [GB] United Kingdom ............... 21342/79

[51] Int. Cl.³ ............................................. C07D 499/80
[52] U.S. Cl. ..................................... 424/270; 424/246; 424/272; 260/245.2 R; 542/420
[58] Field of Search ....................... 424/246, 270, 272; 260/245.2; 542/420

[56] References Cited

U.S. PATENT DOCUMENTS 3,957,764 5/1976 Lund et al. ..................... 260/240 G
4,089,963 5/1978 Bamberg et al. ................ 260/245.2

Primary Examiner—Nicholas S. Rizzo
Attorney, Agent, or Firm—Cushman, Darby & Cushman

[57] ABSTRACT

The present invention relates to hitherto unknown compounds of the general formula I:

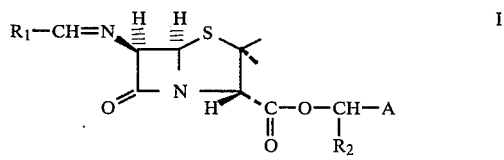

in which $R_1$ stands for a five- to ten-membered azacycloalkyl or azabicycloalkyl residue attached via the nitrogen atom and optionally being substituted by one or two, the same or different, lower alkyl groups; $R_2$ represents a hydrogen atom or a lower alkyl, aryl, or aralkyl radical; and A represents a radical of a β-lactamase inhibitor containing a β-lactam ring as well as a carboxy group, A being connected via the carboxy group.

The present compounds are useful in the treatment of bacterial infections. The new compounds are in particular strongly active against β-lactamase producing bacteria.

25 Claims, 1 Drawing Figure

6-AMIDINOPENICILLANIC ACID DERIVATIVES INCLUDING THE RADICAL OF A β-LACTAMASE INHIBITOR

The present invention relates to hitherto unknown β-lactam compounds including their salts with pharmaceutically acceptable, non-toxic acids, to methods for producing said new compounds, to pharmaceutical compositions containing the new compounds, to dosage units of the compositions, and to methods of treating patients suffering from infectious diseases using said new compounds.

The present invention provides new compounds useful in the treatment of bacterial infections. The new compounds are in particular strongly active against β-lactamase producing bacteria.

The compounds of the invention, which are valuable antibiotics in the human and veterinary practice, are represented by the general formula I:

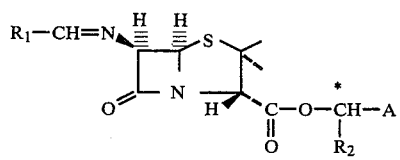

in which $R_1$ stands for a five- to ten-membered azacycloalkyl or azabicycloalkyl residue attached via the nitrogen atom and optionally being substituted by one or two, the same or different, lower alkyl groups, such as methyl, ethyl, propyl, isopropyl, butyl, isobutyl, sec-butyl, and tert-butyl; $R_2$ represents a hydrogen atom or a lower alkyl, aryl or aralkyl radical, and the asterisk in the ester moiety indicates a chiral center in cases where $R_2$ is different from hydrogen; A represents a radical of a β-lactamase inhibitor containing a β-lactam ring as well as a carboxy group, A being connected via the carboxy group. More specifically, A is represented by one of the general formulae II, III, or IV:

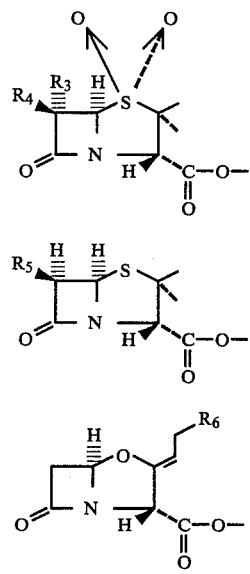

in which $R_3$ stands for a hydrogen or a halogen atom; $R_4$ is a hydrogen atom or an amino or acylamino group, but at least one of $R_3$ and $R_4$ being hydrogen; $R_5$ represents a halogen atom; and $R_6$ stands for a hydroxyl group, or one of the radicals of known clavulanic acid derivatives with β-lactamase inhibitory activity.

Generally, "lower alkyl" stands for a C-1 to C-6 straight or branched alkyl radical, aryl stands for a monocyclic or bicyclic, carbocyclic radical, and acylamino stands for a radical present in the side chain of well-known penicillins.

Of particular interest are compounds in which $R_1$ represents piperidyl-1, hexahydro-1H-azepin-1-yl, hexahydro-1(2H)-azocin-1-yl, octahydro-1H-azonin-1-yl, 2-methyl-hexahydro-1H-azepin-1-yl, 3-methyl-hexahydro-1H-azepin-1-yl, 4-methyl-hexahydro-1H-azepin-1-yl, 2,6-dimethylpiperidyl-1, cis-3-azabicyclo[3.3.0]octyl-3, or cis-8-azabicyclo[4.3.0]-nonyl-8; and $R_2$ represents hydrogen, methyl, ethyl, phenyl, or benzyl.

The possible presence of one or more chiral centers in $R_1$ as well as in the ester moiety (indicated by an asterisk) may give rise to several diastereomeric forms of the compounds of the general formula I. The present invention covers all possible diastereomeric forms of the compound of formula I as well as mixtures thereof.

As stated above, the invention also relates to salts of the esters of formula I with pharmaceutically acceptable, non-toxic acids, e.g. hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, maleic acid, pamoic acid, and p-(dipropylsulfamyl)benzoic acid (probenecide), without these examples being limiting the invention. Also salts with acidic antibiotics are within the scope of the invention. In some instances, it is preferred to use easily soluble salts, whereas for other purposes, it may be appropriate to use an only slightly soluble salt, e.g. in order to obtain a prolonged effect. In particular, a prolonged effect can be obtained by using a salt with probenecid which blocks the tubular excretion of β-lactam compounds.

It is well known that certain 6-amidinopenicillanic acids are valuable antibiotics showing particularly good effect against many gram-negative bacteria. They are, however, insufficiently absorbed when given by mouth and are therefore primarily used by parenteral routes. For oral administration easily hydrolyzable esters, e.g. acyloxyalkyl esters, of these compounds are used, being in contrast to the free acids readily absorbed from the gastrointestinal tract. Such esters may be alkanoyloxyalkyl esters, but include also bis-esters of the 6-amidinopenicillanic acids with aldehyde hydrates. These latter compounds are described in DOS 27 16 172 (German Offenlegungsschrift).

In clinical treatment of bacterial infections it is, however, a serious problem that β-lactamase producing bacteria are occurring with increasing frequency. These enzymes inactivate most β-lactam antibiotics, and it is well recognized that β-lactamases from both gram-positive and gram-negative bacteria contribute significantly to the resistance of bacteria to β-lactam antibiotics.

Several naturally occurring β-lactamase inhibitors including clavulanic acid and the olivanic acids, have been described. More recently, a number of semisynthetic β-lactam compounds, e.g. penicillanic acid 1,1-dioxide, 6α-chloropenicillanic acid 1,1-dioxide, a series of clavulanic acid derivatives, 6β-halopenicillanic acids, such as 6β-bromopenicillanic acid, methicillin sulphone, and quinacillin sulphone, were found to possess similar biological properties. With a few exceptions, these compounds display only weak antibacterial activity against most gram-positive and gram-negative organisms, but are powerful inhibitors of a wide range of β-lactamases. In combination with selected penicillins and cephalosporins, the compounds act synergistically against a variety of β-lactamase producing bacteria because they protect the penicillins and cephalosporins against inactivation.

The results of these studies are summarized in Tables I and II.

TABLE I

Serum concentrations and urinary excretion of mecillinam in fasting volunteers following oral administration of
 A. 100 mg of pivmecillinam hydrochloride in tablets
 B. 128 mg of VD-1825<sup>x</sup> hydrochloride (corresponding to 100 mg of pivmecillinam hydrochloride) in aqueous solution

| | Serum concentrations (μg/ml) | | | | | | | | | | Urinary excretion (% of dose) | | |
|---|---|---|---|---|---|---|---|---|---|---|---|---|---|
| | Hours after administration | | | | | | | | | | | | |
| | 0.25 | | 0.5 | | 1 | | 2 | | 4 | | 0–6 | | 0–24 | |
| Subject | A | B | A | B | A | B | A | B | A | B | A | B | A | B |
| GK | <0.06 | 0.66 | 0.53 | 1.2 | 1.1 | 1.3 | 0.61 | 0.46 | 0.09 | 0.07 | 49 | 54 | 50 | 55 |
| MK | <0.06 | 0.34 | 0.30 | 1.1 | 1.5 | 1.3 | 0.70 | 0.46 | 0.13 | 0.06 | 41 | 42 | 41 | 43 |
| FJ | <0.06 | 1.1 | 0.60 | 1.4 | 1.6 | 1.1 | 0.66 | 0.31 | 0.10 | <0.06 | 37 | 42 | 38 | 43 |
| MM | 0.14 | 0.43 | 0.68 | 1.3 | 2.0 | 1.3 | 0.98 | 0.38 | 0.13 | 0.06 | NS+ | 36 | NS+ | 38 |
| LA | 0.34 | 0.60 | 0.82 | 1.9 | 1.6 | 1.6 | 0.59 | 0.61 | 0.13 | 0.16 | 47 | 42 | 48 | 44 |
| Mean | (0.10) | 0.63 | 0.59 | 1.4 | 1.6 | 1.3 | 0.71 | 0.44 | 0.12 | 0.07 | 43 | 43 | 44 | 45 |

<sup>x</sup>VD-1825 is 1,1-dioxopenicillanoyloxymethyl 6-[(hexahydro-1H-azepin-1-yl)-methylene-amino]penicillanate
<sup>+</sup>No sample As mentioned above, the present invention provides new compounds in particular intended for enteral use and being strongly antibacterially active in vivo. The advantageous effect against β-lactamase producing bacteria is achieved because the compounds contain in one and the same molecule both the moiety of an antibacterially highly active 6-amidinopenicillanic acid and the moiety of a potent β-lactamase inhibitor. However, two prerequisites are necessary to utilize this feature of the new compounds. They must be capable of being absorbed from the gastro-intestinal tract, and during or after the absorption they must be hydrolyzed with liberation of the amidinopenicillanic acid and the β-lactamase inhibitor. It has turned out that both of these prerequisites are fulfilled, and therefore the present compounds are valuable pro-drugs of both the amidinopenicillanic acids and the β-lactamase inhibitors.

Thus, studies in animals and human volunteers have shown that the new compounds are readily absorbed from the gastro-intestinal tract. During or after the absorption they are hydrolyzed with liberation of equimolar amounts of the two components in question, the 6-amidinopenicillanic acid and the β-lactamase inhibitor, giving rise to simultaneous high blood and tissue levels of the two components. Thereby the 6-amidinopenicillanic acids are in the most effective manner protected against inactivation by the β-lactamases.

The efficient absorption and in vivo hydrolysis of the compounds of the invention are illustrated by a study in human volunteers dosed orally with one of the new compounds, namely the hydrochloride of 1,1-dioxopenicillanoyloxymethyl 6-[(hexahydro-1H-azepin-1-yl)-methyleneamino]penicillanate, in the following called VD-1825.

For comparison, the same group of volunteers was also given equimolar amounts of the orally active pivaloyloxymethyl ester of mecillinam<sup>(x)</sup>, pivmecillinam hydrochloride, and potassium penicillanate 1,1-dioxide, respectively.
<sup>(x)</sup>Mecillinam is the generic name for 6-[(hexahydro-1H-azepin-1-yl)-methyleneamino]penicillanic acid.

TABLE II

Urinary excretion in 0 to 6 hours of penicillanic acid 1,1-dioxide in fasting volunteers following oral administration of:
 A. 60 mg of potassium penicillanate 1,1-dioxide (corresponding to 52 mg of penicillanic acid 1,1-dioxide) in aqueous solution
 B. 128 mg of VD-1825 hydrochloride (corresponding to 49.0 mg of penicillanic acid 1,1-dioxide) in aqueous solution

| | Urinary excretion (% of dose) | |
|---|---|---|
| Subject | A | B |
| GK | 2.4 | 78 |
| MK | 3.2 | 86 |
| FJ | 7.7 | 70 |
| MM | 5.2 | 79 |
| LA | 2.9 | 83 |
| Mean | 4.3 | 77 |

It will appear from Table I that oral administration of VD-1825 gives rise to similar serum levels of mecillinam as obtained after an equimolar dose of pivmecillinam. It also appears from Table I that the urinary recovery of mecillinam after administration of VD-1825 is comparable to that following administration of pivmecillinam.

As indicated in Table II, only 4.3% of penicillanic acid 1,1-dioxide were excreted in the urine after oral administration of the corresponding potassium salt. In contrast thereto, administration of an equimolar amount of VD-1825 gave 77% urinary recovery of penicillanic acid 1,1-dioxide, thus again illustrating the efficient absorption of VD-1825.

The efficient absorption and in vivo hydrolysis of the compounds of the invention are further illustrated by a study in eight fasting, healthy human volunteers who received an oral dose of 260 mg of VD-1825, HCl (corresponding to 200 mg of pivmecillinam HCl) in a capsule. After administration, the serum levels of mecillinam and penicillanic acid 1,1-dioxide were determined, and the results appear from FIG. 1. The dashed line indicates serum levels of penicillanic acid 1,1-dioxide, and the full-drawn line indicates serum levels of mecillinam.

It will appear from FIG. 1 that administration of VD-1825, HCl gives rise to simultaneous high levels of mecillinam and β-lactamase inhibitor and further that the latter always is present in approximately the same molar ratio and thus is able to efficiently protect the mecillinam molecule against the influence of β-lactamases.

By using the compounds of the invention the antibacterial spectrum of the 6-amidinopenicillanic acid in question is widely extended, as also β-lactamase producing strains will be susceptible to treatment. Such β-lactamase producing strains are found with increasing frequency and are a serious problem in the clinical therapy. The compounds of the invention will for such purposes be of extreme value.

Therapeutically the new compounds have distinct advantages over mere combinations of the amidinopenicillanic acids and the β-lactamase inhibitors to which they are hydrolyzed, or combinations of orally active esters thereof.

For example, many of the β-lactamase inhibitors, including penicillanic acid 1,1-dioxide, cf. Table II, are absorbed poorly or irregularly from the gastro-intestinal tract. Also, many of the amidinopenicillanic acids, including mecillinam, are incompletely absorbed, when given orally. In addition, individual variations in the rate of absorption of the various amidinopenicillanic acids and β-lactamase inhibitors may in many instances lead to a situation where the active components are not present simultaneously or in the optimum ratio, even if the two drugs are given simultaneously.

Certain easily hydrolyzable esters of amidinopenicillanic acids and β-lactamase inhibitors are absorbed better from the gastro-intestinal tract than the corresponding free acids. However, hydrolysis of such esters in the organism gives rise to the formation of inactive by-products, and although these by-products are relatively non-toxic, it is undesirable to expose the organism to unnecessary metabolites. Another disadvantage by using combinations of easily hydrolyzable esters of the amidinopenicillanic acid derivatives and the β-lactamase inhibitors is that the ester moieties increase the molecular weight of the compounds and consequently the size of the dosage unit. By using the compounds of the invention, the size of the dosage units can be decreased considerably.

In addition, the absorption of such esters will normally not take place simultaneously, even if the compounds are given to the patient at the same time. For instance, the pivaloyloxymethyl ester of mecillinam is being absorbed very rapidly, whereas the sparingly soluble pivaloyloxymethyl ester of the β-lactamase inhibitor penicillanic acid 1,1-dioxide is being absorbed much more slowly.

All of these disadvantages are avoided by using the compounds of the invention.

It has been found that the in vitro synergy between the different β-lactamase inhibitors and various amidinopenicillanic acid derivatives is particularly pronounced when the ratio between the two components is between 3:1 and 1:3. As the various amidinopenicillanic acid derivatives have slightly different biological half-lives and distribution characteristics, the ratio between the liberated components of the new compounds in the organs and tissues may vary to some degree, but will normally be within the above preferred limits.

The present invention also includes methods for the preparation of the new compounds and their salts. According to one method a compound of formula V:

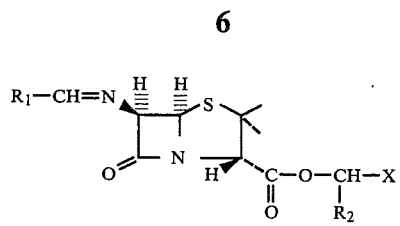

in which formula $R_1$ and $R_2$ are as defined above, and in which X stands for a leaving group, such as a halogen atom, preferably iodine, is reacted with a compound of formula A—M in which A is as defined before, and M is a cation, such as $Na^+$, $K^+$, an ammonium ion, a tri- or a tetraalkylammonium ion, e.g. a tetrabutylammonium ion.

The reaction is performed in a suitable solvent, e.g. dimethylformamide, ethyl acetate, dichloromethane, acetone or hexamethyl phosphoric acid triamide, for a sufficient time and at an adequate temperature with a view to accomplish the desired conversion, usually at a temperature from 0° to 60° C.

The compounds of formula I can also be prepared according to a method in which as a first step a compound of formula A—M is reacted with a compound of formula VI to afford an intermediate of formula VII:

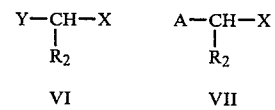

In formulas VI and VII $R_2$, A, and X are as defined before, and Y represents a leaving group, such as bromine or iodine, halosulphonyloxy, e.g. chlorosulphonyloxy, alkylsulphonyloxy, α-haloalkoxysulphonyloxy, or unsubstituted or substituted arylsulphonyloxy, such as benzenesulphonyloxy, tosyloxy, or bromobenzenesulphonyloxy, Y being a better leaving group than X.

The reaction is performed in the same manner as described for the preparation of the known compounds of formula V and takes place in a suitable solvent, e.g. dimethylformamide, ethyl acetate, dichloromethane, acetone or hexamethyl phosphoric acid triamide, usually at a temperature from 0° to 60° C.

In a second step the intermediate of formula VII is reacted with an amidinopenicillanic acid derivative of formula VIII:

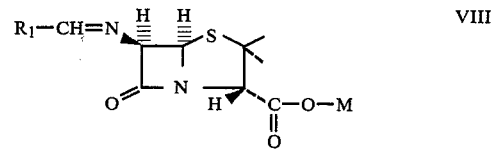

in which $R_1$ and M are as defined above to form an ester of formula I. If desired, the X, in formula VII can in advance be exchanged by a better leaving group.

The above conversions are performed in a reaction-inert organic solvent, e.g. dimethylformamide, ethyl acetate, dichloromethane, acetone or hexamethyl phosphoric acid triamide under conditions mentioned above, and usually at temperatures between 0° C. and 60° C.

Another embodiment of the method comprises a first step in which a compound of formula A—M is reacted with a 6-aminopenicillanic acid ester of formula IX or an amino-protected derivative thereof, e.g. a trialkylsilyl derivative, to afford a compound of formula X:

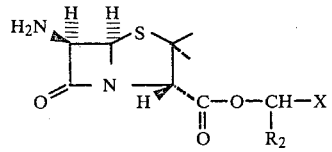

IX

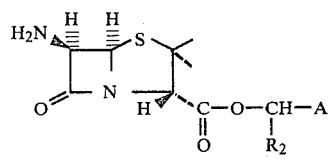

X in which formulae $R_2$, A, and X are as defined before. The reaction is performed in a suitable organic solvent. e.g. dimethylformamide, and preferably at temperatures between 0° C. and 30° C.

Alternatively, the intermediates of formula X can be prepared by reacting 6-aminopenicillanic acid or a salt or an amino-protected derivative thereof with a compound of formula VII.

In a second step a compound of formula X or a trialkylsilyl derivative thereof is reacted with a reactive derivative of an amide or thioamide of formula XI:

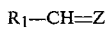    XI in which $R_1$ has the meanings defined above, and Z stands for oxygen or sulphur to yield an ester of formula I.

As examples of reactive derivatives of a compound of formula XI, the following non-limiting types of compounds may be given: iminium chlorides, iminium ethers, iminium thioethers, amide acetals.

The reactions with the said reactive derivatives are well-known to the man skilled in the art for preparing amidinopenicillanic acid derivatives.

In a further embodiment of the method compounds of formula I are prepared by reacting a compound of formula X or a trialkylsilyl derivative thereof with a compound of formula XII:

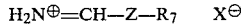    XII in which X and Z are as defined before, and $R_7$ is a lower alkyl or benzyl radical, whereby the hydrogen atoms of the 6-amino group in formula X are replaced by a $R_7$—Z—CH= group. Without isolation of the reaction product, an amine of the formula $R_1$—H, in which $R_1$ has the above meanings, is added to the reaction mixture, whereby a compound of formula I is obtained.

The reaction is preferably performed in an inert organic solvent such as diethyl ether, tetrahydrofuran, ethyl acetate or benzene at room temperature or lower temperatures. The first part of the reaction proceeds rapidly, and after the addition of the amine $R_1$—H, the reaction mixture is placed at room temperature or at lower temperature until the reaction has finished.

The intermediates of formula VII and X are hitherto unknown compounds.

The starting materials of formulas V, VI, VIII, IX, XI, and XII are known or may be prepared by methods analogous to those used for the preparation of similar known compounds.

Most of the starting materials of formula A—M or the corresponding acids are known compounds. New compounds are acids and salts corresponding to A being a radical of formula II in which $R_4$ stands for certain acylamino radicals. The latter compounds are penicillin sulphones, which may be prepared by known methods.

The compounds of formula I can be purified and isolated in usual manner and may be obtained either in the free state or in the form of a salt.

The compounds may in some cases be obtained as diastereomeric mixtures which when desired may be separated by known methods, e.g. chromatography.

It is a further object of the present invention to provide pharmaceutical compositions which are useful in the treatment of infectious diseases in the human and veterinary practice, and which may be used for enteral, parenteral or topical administration.

With this object in view, the compositions of the invention contain as an active component at least one member selected from the group consisting of compounds of the formula I and salts thereof as defined above, together with solid or liquid pharmaceutical carriers and/or diluents.

In the said compositions, the proportion of therapeutically active material to carrier substance can vary between 1% and 95% by weight. The compositions can be worked up to various pharmaceutical forms of presentation, such as tablets, pills, dragees, suppositories, capsules, sustained-release tablets, suspensions and the like containing the compounds of formula I or their atoxic salts, mixed with carriers and/or diluents.

Pharmaceutically acceptable, non-toxic, organic or inorganic, solid or liquid carriers and/or diluents can be used to make up compositions containing the present compounds. Gelatine, lactose, starch, magnesium stearate, talc, vegetable and animal fats and oils, gum, polyalkylene glycol, buffers or other known carriers, auxiliary agents and/or diluents for medicaments are all suitable.

Furthermore, the compositions may contain other therapeutically active components which can appropriately be administered together with the present compounds in the treatment of infectious diseases, such as other antibacterials, antitussiva, pain-relieving drugs, probenecid, etc. In particular, antibacterials, such as penicillins or cephalosporins, which act synergistically with one or both of the active components formed by in vivo hydrolysis of the compounds of the invention, are appropriate.

The compounds of formula I can be used either as such or in the form of a salt. The compounds as such are only slightly soluble in water whereas many of the salts, e.g. the hydrochlorides, are readily soluble in water.

As indicated above, the present compounds may be worked up to pharmaceutical forms of presentation including suspensions and non-aqueous ointments. A pharmaceutical preparation for oral treatment may be in the form of a suspension of one of the present compounds, the preparation containing from 10 mg to 100 mg per ml of the vehicle.

Another object of the invention resides in the selection of a dose of the compounds of the invention and a dosage unit of the compositions of the invention which dose and dosage unit can be administered so that the desired activity is achieved without simultaneous secondary effects. In the human therapy, the present compounds are conveniently administered (to adults) in dosage units of the compositions containing not less than 50 mg and up to 2500 mg, preferably from 100 mg to 1000 mg calculated as the compound of formula I.

By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents, carriers, solvents and/or auxiliary agents.

In the form of a dosage unit, the compound may be administered once or more times a day at appropriate intervals, always depending, however, on the condition of the patient, and in accordance with the prescription made by the medical practitioner.

Thus a daily dose will preferably be an amount of from 0.25 to 15 g of a compound of formula I or an equivalent amount of a salt thereof as defined before, which conveniently can be divided into several single doses.

In the continuous therapy of patients suffering from infectious diseases, the tablets or capsules are the appropriate form of pharmaceutical preparation, if desired in the form of sustained-release formulations.

In the veterinary practice the above pharmaceutical compositions may also be used, preferably in the form of dosage units containing from 50 mg up to 25 g of the compound of formula I or a corresponding amount of a salt thereof.

For the treatment of mammary disorders, especially bovine mastitis, the antibacterial agent can be administered by the intramammary route in liquid or semiliquid form, such as an ointment, or together with a substantially water-insoluble and oil-insoluble binding agent in the form of granules.

Still another object of the invention is to provide a method of treating patients suffering from infectious diseases, the method comprising administering to adult patients an effective amount of a compound of formula I, either as such or in the form of a salt as defined before, and preferably, in the form of the dosage units aforesaid. The compounds of formula I are typically administered in amounts of 3–200 mg/kg body weight of the patient/day, corresponding to, for adult human patients, from 0.25 g to 15 g per day, or an equivalent amount of a salt as defined before of a compound of formula I.

In the treatment of patients, the present compounds can be administered either alone or together with other therapeutically active compounds, e.g. probenecid, which aid in combatting the bacterial infection. Such combined treatment can be performed with formulations containing more or all of the therapeutically active compounds, or these may be administered in separate formulations, these being given simultaneously or with suitable intervals.

In the treatment of patients, the daily dose is administered either at one time, or in divided dosages, e.g. two, three or four times a day.

In the following "Preparations" the methods for preparing new starting materials and intermediates are more specifically described.

PREPARATION 1

6α-Bromopenicillanic acid 1,1-dioxide

To a stirred solution of potassium permanganate (1.90 g, 12 mmol) in water (35 ml) and acetic acid (1.36 ml, 24 mmol) was added dropwise at 0°–5° C. an icecold solution of potassium 6α-bromopenicillanate (1.91 g, 6 mmol) in water (25 ml). After the addition was finished (about 15 minutes), the mixture was stirred for another 20 minutes at the low temperature. The cooling-bath was removed, and to the mixture was added solid sodium pyrosulphite (1.52 g, 8 mmol) to reduce excess oxidation reagent. Precipitated manganese oxides were filtered off, and to the filtrate (about 60 ml) was added solid sodium chloride (20 g) and ethyl acetate (50 ml). The pH of the mixture was adjusted to 1.5 by addition of 4 N hydrochloric acid with stirring, and the organic phase was separated. The aqueous phase was reextracted with ethyl acetate (25 ml), and the combined organic extracts were washed with saturated aqueous sodium chloride, dried, and evaporated in vacuo. The amorphous residue thus obtained was crystallized from ether-diisopropyl ether to afford 6α-bromopenicillanic acid 1,1-dioxide, melting point: 124°–127° C.

A crystalline potassium salt of the above compound was obtained by addition of 1 M potassium 2-ethylhexanoate in acetone (3.6 ml) to a stirred solution of 6α-bromopenicillanic acid 1,1-dioxide (0.94 g, 3 mmol) in acetone (12 ml).

The NMR spectrum of potassium 6α-bromopenicillanate 1,1-dioxide (CD$_3$OD) showed signals at δ=1.48 (s, 3H; 2-CH$_3$), 1.59 (s, 3H; 2-CH$_3$), 4.48 (s, 1H; 3-H), 5.10 (d, J=2 Hz, 1H; 6-H), and 5.35 (d, J=2 Hz, 1H; 5-H) ppm. Tetramethylsilane was used as internal reference.

PREPARATION 2

6α-Chloropenicillanic acid 1,1-dioxide

By substituting potassium 6α-chloropenicillanate for the potassium 6α-bromopenicillanate in the procedure of Preparation 1, 6α-chloropenicillanic acid 1,1-dioxide was obtained as crystals from diisopropyl ether, melting point: 134°–137° C.

The NMR spectrum (CDCl$_3$) showed signals at δ=1.50 (s, 3H; 2-CH$_3$), 1.64 (s, 3H; 2-CH$_3$), 4.46 (s, 1H; 3-H), 4.70 (d, J=1.5 Hz, 1H; 6-H), and 5.18 (d, J=1.5 Hz, 1H; 5-H) ppm. Tetramethylsilane was used as internal reference.

A crystalline potassium salt of the above compound was obtained by addition of an equimolar amount of 0.8 M potassium 2-ethylhexanoate in acetone to a stirred solution of 6α-chloropenicillanic acid 1,1-dioxide in acetone.

PREPARATION 3

Chloromethyl penicillanate 1,1-dioxide

To a solution of penicillanic acid 1,1-dioxide (1.17 g, 5 mmol) in dimethylformamide (7.5 ml) was added triethylamine (0.98 ml, 7 mmol) and chloroiodomethane (2.18 ml, 30 mmol), and the mixture was stirred at room temperature for 4 hours. After dilution with ethyl acetate (30 ml), the mixture was washed with water (3×10 ml) followed by saturated aqueous sodium chloride (5 ml), dried, and evaporated in vacuo to leave the desired compound as a yellowish oil, which crystallized from ether-petroleum ether, melting point: 94°–96° C.

The NMR spectrum (CDCl$_3$) showed signals at δ=1.47 (s, 3H; 2-CH$_3$), 1.66 (s, 3H; 2-CH$_3$), 3.53 (d, J=3 Hz, 2H; 6α-H and 6β-H), 4.46 (s, 1H; 3-H), 4.68 (t, J=3 Hz, 1H; 5-H), and 5.85 (ABq, J=6 Hz, 2H; OCH$_2$Cl) ppm. Tetramethylsilane was used as internal reference.

PREPARATION 4

1-Chloroethyl penicillanate 1,1-dioxide

Following the procedure of Preparation 3, but substituting 1-chloro-1-iodoethane for the chloroiodomethane and increasing the reaction time to 16 hours, crude 1-chloroethyl penicillanate, 1,1-dioxide was obtained as a yellow oil which could be purified by dry column chromatography on silica gel (ethyl acetate-petroleum ether, 7:3).

PREPARATION 5

Chloromethyl 6α-bromopenicillanate 1,1-dioxide

By substituting 6α-bromopenicillanic acid 1,1-dioxide for the penicillanic acid 1,1-dioxide in the procedure of Preparation 3, chloromethyl 6α-bromopenicillanate 1,1-dioxide was obtained as a yellowish oil.

The NMR spectrum (CDCl$_3$) showed signals at $\delta = 1.48$ (s, 3H; 2-C$\underline{H}_3$), 1.64 (s, 3H; 2-C$\underline{H}_3$), 4.46 (s, 1H; 3-$\underline{H}$), 4.71 (d, J=1.5 Hz, 1H; 6-$\underline{H}$), 5.17 (d, J=1.5 Hz, 1H; 5$\underline{H}$), and 5.80 (ABq, J=6 Hz, 2H; OC$\underline{H}_2$Cl) ppm. TMS was used as internal reference.

PREPARATION 6

Chloromethyl 6β-bromopenicillanate

By substituting potassium 6β-bromopenicillanate for the penicillanic acid 1,1-dioxide and the triethylamine in the procedure of preparation 3, chloromethyl 6α-brompenicillanate was obtained as a viscous oil.

PREPARATION 7

Chloromethyl clavulanate

Following the procedure of Preparation 3, but substituting sodium clavulanate for the penicillanic acid 1,1-dioxide and the triethylamine, chloromethyl clavulanate was obtained.

PREPARATION 8

Chloromethyl penicillanate 1,1-dioxide

To a suspension of potassium penicillanate 1,1-dioxide (1.08 g) in dimethylformamide (12 ml) was added bis-chloromethyl sulphate (1.6 g), and the mixture was stirred at room temperature for 45 minutes. After dilution with ethyl acetate (50 ml), the mixture was washed with water followed by aqueous sodium bicarbonate, dried and evaporated in vacuo to leave an oil which was purified by chromatography on silica gel to yield the desired compound, identical with the compound described in preparation 3.

PREPARATION 9

Chloromethyl 6α-chloropenicillanate 1,1-dioxide

By substituting 6α-chloropenicillanic acid 1,1-dioxide for the penicillanic acid 1,1-dioxide in the procedure of Preparation 3, chloromethyl 6α-chloropenicillanate 1,1-dioxide was obtained as a viscous oil.

The NMR spectrum (CDCl$_3$) showed signals at $\delta = 1.48$ (s, 3H; 2-C$\underline{H}_3$), 1.64 (s, 3H; 2-C$\underline{H}_3$), 4.47 (s, 1H; 3-H), 4.68 (d, J=1.5 Hz, 1H; 6-$\underline{H}$), 5.17 (d, J=1.5 Hz, 1$\underline{H}$; 5$\underline{H}$), and 5.81 (ABq, J=6 Hz, 2H; OC$\underline{H}_2$Cl) ppm. TMS was used as internal reference.

PREPARATION 10

Iodomethyl penicillanate 1,1-dioxide

To a solution of chloromethyl penicillanate 1,1-dioxide (5.6 g, 20 mmol) in acetone (45 ml) was added sodium iodide (9 g), and the mixture was stirred at room temperature for 16 hours. Precipitated sodium chloride (1.15 g) was filtered off, the solvent was removed in vacuo, and the residue thus obtained was treated with ethyl acetate-ether (1:1). Insoluble sodium iodide (6 g) was filtered off, and the filtrate was evaporated at reduced pressure.

The residual oil was purified by column chromatography on silica gel (ethyl acetate-n-hexan, 4:6) to yield the title compound as colourless crystals from ether, melting point: 101°–102° C.

PREPARATION 11

6β-Aminopenicillanic acid 1,1-dioxide hydrate

A. 6β-Benzyloxycarbonylaminopenicillanic acid 1,1-dioxide

To a stirred solution of 6β-benzyloxycarbonylaminopenicillanic acid (63.5 g) and potassium hydrogen carbonate (18.1 g) in water (1125 ml) was slowly (about 45 minutes) at 0° C. added a solution of potassium permanganate (38 g) in water (915 ml). During the oxidation, a pH of 6.5 was maintained in the reaction mixture by addition of dilute sulphuric acid. Insoluble material was removed by filtration, and the filtrate was extracted with ethyl ether. The resulting aqueous phase was filtered again and, after addition of ethyl acetate (600 ml), acidified to pH 2.5 with stirring. The organic layer was separated, and the aqueous phase was extracted with additional ethyl acetate (2×300 ml). After drying, the combined ethyl acetate extracts were evaporated in vacuo. The residue was recrystallized from ethyl acetate (250 ml)-petroleum ether (500 ml) to yield the pure compound, melting point: 153°–154° C.; $[\alpha]_D^{20}$: +146.9° (c=1, 96% C$_2$H$_5$OH).

B. 6β-Aminopenicillanic acid 1,1-dioxide hydrate

A filtered solution of 6β-benzyloxycarbonylaminopenicillanic acid 1,1-dioxide (15.3 g) and potassium hydrogen carbonate (4 g) in water (160 ml) was hydrogenated over 10% Pd/BaSO$_4$ (5 g) for 4 hours at slightly elevated pressure. After filtration and extraction with ethyl ether (100 ml), the pH of the ice-cold aqueous solution was adjusted to 2.5. The precipitate thus formed was filtered off, washed with water, and air-dried. Recrystallization from dimethylformamide-water afforded the pure monohydrate; melting point: 199°–200° C. (dec.); $[\alpha]_D^{20}$: +252.9° (c=1, dimethylformamide).

PREPARATION 12

Chloromethyl 1,1-dioxopenicillanate

To a mixture of potassium 1,1-dioxopenicillanate (2.7 g, 10 mmol), potassium hydrogen carbonate (6.0 g, 60 mmol) and tetrabutylammonium hydrogen sulphate (0.34 g, 1 mmol) in water (10 ml) and dichloromethane (15 ml), chloromethyl chlorosulphate (1.5 ml) was added. After stirring for 1 hour at 30° C., the mixture was filtered and the organic layer was separated and dried (sodium sulphate). After dilution with propanol-2 (25 ml), the solution was concentrated to about 10 ml in vacuo and left at 5° C. for 1 hour. The crystals were filtered off, washed with cold propanol-2 and dried in vacuo to give the title compound as colourless crystals with a melting point of 94°–96° C.

PREPARATION 13

1-Chloroethyl 1,1-dioxopenicillanate

To a mixture of potassium 1,1-dioxopenicillanate (40.7 g, 0.15 mol), silver nitrate (25.5 g, 0.15 mol), and silver oxide (7.5 g) in acetonitrile (750 ml), 1-chloro-1-iodoethane (42 ml) was added. After stirring for 48 hours, at ambient temperature, the silver salts were filtered off, and the filtrate taken to dryness in vacuo. The residue was dissolved in ethyl acetate (200 ml), and the solution was washed with saturated aqueous sodium chloride, filtered, dried, and evaporated in vacuo. Chromatography of the residue on silica gel (hexane-ethyl acetate, 3:2) gave the title compound as a crystalline mixture of the two diastereomers with m.p. 130°–132° C.

PREPARATION 14

1-Iodoethyl 1,1-dioxopenicillanate

To a solution of 1-chloroethyl 1,1-dioxopenicillanate (30 g, ~0.1 mol) in acetone (100 ml), sodium iodide (30 g, 0.2 mol) was added, and the mixture was stirred at ambient temperature for 3 days. Aqueous sodium thiosulphate was added, and the acetone was removed in vacuo. The separated oil was dissolved in ethyl acetate, and the solution was washed with water, dried and evaporated in vacuo. The residual oil was chromatographed on silica gel (hexane-ethyl acetate, 3:1) to give a crystalline mixture (m.p. 134°–36° C.) of the diastereomeric 1-iodoethyl and 1-chloroethyl esters, containing 40% of the iodo compound, according to the microanalytical determination of iodine.

PREPARATION 15

Chloromethyl 6β-bromopenicillanate

To a stirred solution of potassium 6β-bromopenicillanate (0.96 g, 3 mmol) and potassium bicarbonate (1.80 g, 18 mmol) in water (9 ml) and ethyl acetate (9 ml) was added tetrabutylammonium hydrogen sulphate (0.10 g, 0.3 mmol), followed by chloromethyl chlorosulphonate (0.45 ml. 4.5 mmol), and the mixture was stirred at room temperature for 1.5 hours. The organic phase was separated, and the aqueous phase re-extracted with ethyl acetate (9 ml). The combined organic extracts were washed with water (2×5 ml), dried, and concentrated to about 5 ml at reduced pressure. The concentrate was subjected to dry column chromatography on silica gel (petroleum ether-ethyl acetate, 9:1) to afford pure chloromethyl 6β-bromopenicillanate as an almost colourless oil.

The NMR spectrum (CDCl$_3$) showed signals at δ=1.54 (s, 3H; 2-C$\underline{H}_3$), 1.70 (s, 3H; 2-C$\underline{H}_3$), 4.54 (s, 1H; 3-$\underline{H}$), 5.35 and 5.59 (2d, J=4 Hz, 2H; 5-$\underline{H}$ and 6-$\underline{H}$), and 5.77 (ABq, J=5 Hz, 2H; OC$\underline{H}_2$Cl) ppm. Tetramethylsilane was used as internal reference.

PREPARATION 16

Iodomethyl 6β-bromopenicillanate

To a solution of chloromethyl 6β-bromopenicillanate (0.82 g, 2.5 mmol) in acetone (5 ml) was added solid sodium iodide (0.75 g, 5.0 mmol), and, after protection from light, the mixture was stirred at room temperature for 24 hours. Precipitated sodium chloride was filtered off, washed with acetone (2×1 ml), and the filtrate was evaporated in vacuo to leave an oily residue which was redissolved in ethyl acetate (20 ml). The resulting solution was washed with water (2×10 ml), dried (MgSO$_4$), and, following concentration to about 5 ml at reduced pressure, subjected to column chromatography on silica gel using petroleum ether-ethyl acetate, 9:1, as the eluent. Fractions containing the pure title compound, as revealed by thin-layer chromatography (TLC), were combined and evaporated in vacuo to yield iodomethyl 6β-bromopenicillanate as a slightly yellowish oil.

The NMR spectrum showed signals at δ=1.55 (s, 3H; 2-C$\underline{H}_3$), 1.69 (s, 3H; 2-C$\underline{H}_3$), 4.50 (s, 1H; 3-$\underline{H}$), 5.34 and 5.57 (2d, J=4 Hz, 2H; 5-$\underline{H}$ and 6-$\underline{H}$), and 5.97 (ABq, J=5 Hz, 2H; OC$\underline{H}_2$I) ppm. Tetramethylsilane was used as internal reference.

PREPARATION 17

Chloromethyl 1,1-dioxo-6β-(2,6-dimethoxybenzamido)penicillanate

Chloromethyl chlorosulphate (1.8 ml, 18 mmol) was added during 20 minutes at room temperature to a mixture of 1,1-dioxo-6β-(2,6-dimethoxybenzamido)penicillanic acid (methicillin sulphone; 6.2 g, 15 mmol), potassium hydrogen carbonate (8.7 g, 87 mmol) and tetrabutylammonium hydrogen sulphate (0.51 g, 1.5 mmol) in water (15 ml) and dichloromethane (15 ml).

After stirring for a further 15 minutes, the organic phase was separated, dried, and evaporated in vacuo to leave an oil which crystallized from 96% ethanol to yield colourless crystals with m.p. 142°–143° C. (dec). Two recrystallizations from acetone-water gave the analytical sample with m.p. 154°–155° C. (dec); $[\alpha]_D^{20}$: +195° (c=1, CHCl$_3$).

PREPARATION 18

Iodomethyl 1,1-dioxo-6β-(2,6-dimethoxybenzamido)penicillanate

Sodium iodide (3 g, 20 mmol) was added to a solution of chloromethyl 1,1-dioxo-6β-(2,6-dimethoxybenzamido)penicillanate (2.31 g, 5 mmol) in acetone (10 ml), and the mixture was stirred overnight at room temperature. Addition of water precipitated the title compound as crystals which were collected by filtration and dried in vacuo; m.p. 153°–156° C. (dec).

The product was dissolved in a mixture of acetone and 96% ethanol, the acetone was removed in vacuo and the desired compound crystallized. By repeating this procedure the m.p. was raised to 169°–170° C. (dec.); $[\alpha]_D^{20}$: +197° (c=1, CHCl$_3$).

PREPARATION 19

Chloromethyl 1,1-dioxo-6α-chloropenicillanate

By substituting potassium 1,1-dioxo-6α-chloropenicillanate for the potassium 6β-bromopenicillanate in the procedure of Preparation 15, the title compound was obtained as colourless crystals from ether-diisopropyl ether; melting point: 111°–113° C.; $[\alpha]_D^{20}$+210° (c=0.5, CHCl$_3$).

PREPARATION 20

Iodomethyl 1,1-dioxo-6α-chloropenicillanate

By substituting chloromethyl 1,1-dioxo-6α-chloropenicillanate for the chloromethyl 6β-bromopenicillanate in the procedure of Preparation 16, the title compound was obtained as a colourless foam.

The NMR spectrum (CDCl$_3$) showed dignals at δ=1.49 (s, 3H; 2-C$\underline{H}_3$), 1.62 (s, 3H; 2-C$\underline{H}_3$), 4.41 (s, 1H; 3-$\underline{H}$), 4.66 and 5.16 (2d, J=1.5 Hz, 2H; 5-$\underline{H}$ and 6-$\underline{H}$), and 6.01 (ABq, J=5 Hz, 2H; OCH$_2$I) ppm. Tetramethylsilane was used as internal reference.

PREPARATION 21

Chloromethyl 1,1-dioxo-6α-bromopenicillanate

By substituting potassium 1,1-dioxo-6α-bromopenicillanate for the potassium 6β-bromopenicillanate in the prodecure of Preparation 15, the title compound was obtained as colourless crystals from ether-diisopropyl ether; melting point: 92°–93° C.; [α]$_D^{20}$+185° (c=0.5, CHCl$_3$).

PREPARATION 22

Iodomethyl 1,1-dioxo-6α-bromopenicillanate

By substituting chloromethyl 1,1-dioxo-6α-bromopenicillanate for the chloromethyl 6β-bromopenicillanate in the procedure of Preparation 16, the title compound was obtained as a colourless foam which failed to crystallize.

The NMR spectrum (CDCl$_3$) showed signals at δ=1.49 (s, 3H; 2-CH$_3$), 1.63 (s, 3H; 2-CH$_3$), 4.41 (s, 1H; 3-H), 4.70 and 5.16 (2d, J=1.5 Hz, 2H; 5-H and 6-H), and 6.01 (ABq, J=5 Hz, 2H; OCH$_2$I) ppm. Tetramethylsilane was used as internal reference.

PREPARATION 23

Chloromethyl 6β-iodopenicillanate

By substituting potassium 6β-iodopenicillanate for the potassium 6β-bromopenicillanate in the procedure of Preparation 15, the title compound was obtained as a slightly yellowish oil.

The NMR spectrum (CDCl$_3$) showed signals at δ=1.52 (s, 3H; 2-CH$_3$), 1.71 (s, 3H; 2-CH$_3$), 4.55 (s, 1H; 3-H), 5.40 and 5.63 (2d, J=3.5 Hz, 2H; 5-H and 6-H), and 5.78 (Abq, J=5.5 Hz, 2H; OCH$_2$Cl) ppm. Tetramethylsilane was used as internal reference.

PREPARATION 24

Iodomethyl 6β-iodopenicillanate

By substituting chloromethyl 6β-iodopenicillanate for the chloromethyl 6β-bromopenicillanate in the procedure of Preparation 16, the title compound was obtained as a yellowish oil.

The NMR spectrum (CDCl$_3$) showed signals at δ=1.53 (s, 3H; 2-CH$_3$), 1.70 (s, 3H; 2-CH$_3$), 4.53 (s, 1H; 3-H), 5.39 and 5.61 (2d, J=3.5 Hz, 2H; 5-H and 6-H), and 6.00 (ABq, J=5.5 Hz, 2H; OCH$_2$I) ppm. Tetramethylsilane was used as internal reference.

PREPARATION 25

Chloromethyl 6β-chloropenicillanate

By substituting potassium 6β-chloropenicillanate for the potassium 6β-bromopenicillanate in the procedure of Preparation 15, the title compound was obtained as a colourless oil.

The NMR spectrum (CDCl$_3$) showed signals at δ=1.53 (s, 3H; 2-CH$_3$), 1.69 (s, 3H; 2-CH$_3$), 4.54 (s, 1H; 3-H), 5.24 and 5.62 (2d, J=4 Hz, 2H; 5-H and 6-H), and 5.80 (ABq, J=5 Hz, 2H; OCH$_2$Cl) ppm. Tetramethylsilane was used as internal reference.

PREPARATION 26

Iodomethyl 6β-chloropenicillanate

By substituting chloromethyl 6β-chloropenicillanate for the chloromethyl 6β-bromopenicillanate in the procedure of Preparation 16, the title compound was obtained as a slightly yellowish oil.

The NMR spectrum (CDCl$_3$) showed signals at δ=1.52 (s, 3H; 2-CH$_3$), 1.69 (s, 3H; 2-CH$_3$), 4.52 (s, 1H; 3-H), 5.22 and 5.58 (2d, J=4 Hz, 2H; 5-H and 6-H), and 5.99 (ABq, J=5 Hz, 2H; OCH$_2$I) ppm. Tetramethylsilane was used as internal reference.

PREPARATION 27

Chloromethyl 6β-bromopenicillanate

A. Chlormoethyl 6,6-dibromopenicillanate

By substituting potassium 6,6-dibromopenicillanate for the potassium 6β-bromopenicillanate in the procedure of Preparation 15, the title compound was obtained as a slightly yellowish oil which crystallized from ether-diisopropyl ether; melting point: 105°–107° C.; [α]$_D^{20}$: +206° (c=0.5, CHCl$_3$).

The NMR spectrum (CDCl$_3$) showed signals at δ=1.54 (s, 3H; 2-CH$_3$), 1.66 (s, 3H; 2-CH$_3$), 4.60 (s, 1H; 3-H), 5.80 (ABq, J=5 Hz, 2H; OCH$_2$Cl), and 5.83 (s, 1H, 5-H) ppm. Tetramethylsilane was used as internal reference.

B. Chloromethyl 6β-bromopenicillanate

To a stirred solution of chloromethyl 6,6-dibromopenicillanate (1.63 g, 4 mmol) in dry benzene (40 ml) was added under nitrogen at 0° C. tri-n-butyltin hydride (1.16 g, 4 mmol). After stirring at room temperature for 18 hours, the mixture was evaporated in vacuo. The residual oil was purified by dry column chromatography on silica gel (petroleum ether-ethyl acetate, 85:15) to yield pure chloromethyl 6β-bromopenicillanate as a slightly yellowish oil.

The NMR spectrum of the product was identical with that of the compound described in Preparation 15.

PREPARATION 28

Bromomethyl 1,1-dioxopenicillanate

To a solution of sodium bromide (1.0 g) in N,N-dimethylformamide (10 ml) was added chloromethyl 1,1-dioxopenicillanate (0.28 g, 1 mmol), and the mixture was stirred at room temperature for 20 hours. After dilution with ethyl acetate (50 ml), the mixture was washed with water (4×10 ml), dried, and evaporated in vacuo. The residue was purified by column chromatography on silica gel to yield the desired compound as a yellowish oil.

The NMR spectrum (CDCl$_3$) showed signals at δ=1.49 (s, 3H; 2-CH$_3$), 1.64 (s, 3H; 2-CH$_3$), 3.52 (m, 2H; 6-H, 4.47 (s, 1H; 3-H), 4.75 (m, 1H; 5-H), and 5.98 (ABq, J=4.5 Hz, 2H;, OCH$_2$Br) ppm. TMS was used as internal reference.

The invention will be further described in the following Examples which are not to be construed as limiting the invention.

EXAMPLE 1

1,1-Dioxopenicillanoyloxymethyl 6-[(hexahydro-1H-azepin-1-yl)-methyleneamino]-penicillanate hydrochloride To a solution of chloromethyl 6-[(hexahydro-1H-azepin-1-yl)-methyleneamino]penicillanate (1.87 g, 5 mmol) in dimethylformamide (25 ml) was added potassium penicillanate 1,1-dioxide (1.36 g, 5 mmol), and the mixture was stirred at room temperature for 48 hours. Ethyl acetate (75 ml) was added, and the mixture was washed with water (4×25 ml) to remove dimethylformamide. The remaining organic phase was dried and decolourized by stirring with charcoal. After removal of the charcoal by filtration and concentration of the filtrate to about 30 ml, water (25 ml) was added, and the apparent pH of the mixture was adjusted to 2.6 by addition of 4 N hydrochloric acid with stirring. The aqueous phase was separated and freeze-dried to yield the desired compound as an amorphous powder.

The NMR-spectrum (D$_2$O) showed signals at $\delta = 1.48$ and 1.55 (2s, 6H; C(C$\underline{H}_3$)$_2$), 1.60 and 1.72 (2s, 6H; C(C$\underline{H}_3$)$_2$), 1.68 (b, 8H; C$\underline{H}_2$C$\underline{H}_2$C$\underline{H}_2$), 3.65 (m, 6H; C$\underline{H}_2$NC$\underline{H}_2$, 6α-$\underline{H}$ and 6β-$\underline{H}$), 4.68 (s, 1H; 3-$\underline{H}$), 4.75 (s, 1H; 3-$\underline{H}$), 5.08 (dd, J$^1$=4 Hz, J$^2$=2 Hz, 1H; 5-$\underline{H}$), 5.56 (d, J=4 Hz, 1H; 6-$\underline{H}$), 5.68 (d, J=4 Hz, 1H; 5-$\underline{H}$), 6.02 (s, 2H; OC$\underline{H}_2$O), and 8.03 (s, 1H; N—C$\underline{H}$=N) ppm. Tetramethylsilane was used as external reference.

To a solution of the above product (0.5 g) in methanol (1.5 ml) was added isopropanol until turbidity occurred, and crystallization was induced by scratching. After being kept in the refrigerator for 24 hours, the crystals were filtered off, washed with isopropanol, and dried in vacuo to give the title compound as a colourless, crystalline product showing an ill-defined melting point (slow decomposition above 120° C.).

The IR-spectrum (KBr) showed bands at $\nu = 1690$ and 1790 (broad) cm$^{-1}$.

EXAMPLE 2

1,1-Dioxopenicillanoyloxymethyl 6-[(hexahydro-1H-azepin-1-yl)-methyleneamino]-penicillanate hydrochloride Chloromethyl penicillanate 1,1-dioxide (1.41 g, 5 mmol) was added to a solution of 6-[(hexahydro-1H-azepin-1-yl)methyleneamino]penicillanic acid (1.63 g, 5 mmol) and triethylamine (0.7 ml, 5 mmol) in dimethylformamide (25 ml), and the mixture was stirred at room temperature for 16 hours. After dilution with ethyl acetate (75 ml), the mixture was washed with water (4×20 ml), and the remaining organic phase was dried and decolourized with charcoal. The charcoal was removed by filtration, and to the filtrate was added water (35 ml). The apparent pH of the mixture was adjusted to 2.8 by addition of 2 N hydrochloric acid with stirring. The aqueous phase was separated and freeze-dried to afford an amorphous compound identical with that obtained in Example 1.

EXAMPLES 3–11

By substituting the amidinopenicillanic acids listed in Table 1 below for the 6-[(hexahydro-1H-azepin-1-yl)-methyleneamino]penicillanic acid in the procedure of Example 2, the corresponding compounds of formula I were obtained.

TABLE 1

Starting Material

R$_1$—CH=N—[penicillanic acid structure]—CO$_2$H

| Example | R$_1$ |
|---|---|
| 3 | piperidyl-1 |
| 4 | 2,6-dimethylpiperidyl-1 |
| 5 | 2-methyl-hexahydro-1H-azepin-1-yl |
| 6 | 3-methyl-hexahydro-1H-azepin-1-yl |
| 7 | 4-methyl-hexahydro-1H-azepin-1-yl |
| 8 | hexahydro-1(2H)-azocin-1-yl |

TABLE 1-continued

Starting Material

R$_1$—CH=N—[penicillanic acid structure]—CO$_2$H

| Example | R$_1$ |
|---|---|
| 9 | octahydro-1H-azonin-1-yl |
| 10 | cis-3-azabicyclo[3.3.0]octyl-3 |
| 11 | cis-8-azabicyclo[4.3.0]nonyl-8 |

EXAMPLE 12

1-(1,1-Dioxopenicillanoyloxy)ethyl 6-[(hexahydro-1H-azepin-1-yl)-methyleneamino]-penicillanate hydrochloride By substituting 1-chloroethyl penicillanate 1,1-dioxide for the chloromethyl penicillanate 1,1-dioxide in the procedure of Example 2, 1-(1,1-dioxopenicillanoyloxy)ethyl 6-[(hexahydro-1H-azepin-1-yl)-methyleneamino]-penicillanate hydrochloride was obtained as a colourless foam.

EXAMPLE 13

1,1-Dioxopenicillanoyloxymethyl 6-[(hexahydro-1H-azepin-1-yl)-methyleneamino]-penicillanate hydrochloride To a cooled mixture of 6-[(hexahydro-1H-azepin-1-yl)-methyleneamino]penicillanic acid (5.85 g, 18 mmol) and tetrabutylammonium hydrogen sulphate (6.12 g, 18 mmol) in dichloromethane (35 ml) and water (35 ml) was added 2 N aqueous sodium hydroxide (18 ml) with stirring. The organic layer was separated, the aqueous phase was re-extracted with dichloromethane (15 ml), and the combined dichloromethane extracts were dried (MgSO$_4$) and evaporated in vacuo. The colourless oil thus obtained was dissolved in ethyl acetate (100 ml), and the resulting solution concentrated to about half the volume at reduced pressure. To the concentrate was added in one portion a solution of iodomethyl penicillanate 1,1-dioxide (5.6 g, 15 mmol), and the mixture was stirred at room temperature for 10 minutes. Precipitated tetrabutylammonium iodide was filtered off, to the filtrate was added water (75 ml), and the apparent pH of the stirred mixture was adjusted to 3.0 with 1 N hydrochloric acid at 5° C. The aqueous phase was separated, and under a layer of ethyl acetate (50 ml) the pH was adjusted to 7.2 by addition of 0.5 M aqueous sodium hydrogen carbonate with stirring. After separation of the organic layer, water (50 ml) was added and the pH of the stirred mixture was adjusted to 3.0 with 1 N hydrochloric acid. The aqueous phase was separated and freeze-dried to yield the title compound as colourless, amorphous powder.

A solution of the above product (5 g) in ethanol (15 ml) was diluted with isopropanol (about 20 ml) until turbidity and seeded. After stirring at room temperature for about 1 hour, a heavy crystalline precipitate had formed. The mixture was gradually diluted with isopropanol (40 ml) and kept at 5° C. for 3 hours. The precipitate was filtered off, washed with isopropanol followed by ether, and dried in vacuo to give 1,1-dioxopenicillanoyloxymethyl 6-[(hexahydro-1H-azepin-1-yl)-methyleneamino]penicillanate hydrochloride as colourless crystals with an ill-defined melting point (slow decomposition above 120° C.), identical with the product described in Example 1.

EXAMPLE 14

Clavulanoyloxymethyl 6-[(hexahydro-1H-azepin-1-yl)-methyleneamino]-penicillanate hydrochloride.

By substituting sodium clavulanate for the potassium penicillanate 1,1-dioxide in the procedure of Example 1 and reducing the reaction time to 16 hours, the desired compound was obtained as a yellowish foam.

EXAMPLE 15

1,1-Dioxo-6α-chloropenicillanoyloxymethyl 6-[(hexahydro-1H-azepin-1-yl)-methyleneamino]-penicillanate hydrochloride.

By following the procedure of Example 2, but substituting chloromethyl 6α-chloropenicillanate, 1,1-dioxide for the chloromethyl penicillanate 1,1-dioxide, the title compound was obtained as a yellowish powder.

EXAMPLE 16

6β-Bromopenicillanoyloxymethyl 6-[(hexahydro-1H-azepin-1-yl)-methyleneamino]-penicillanate hydrochloride.

By substituting chloromethyl 6β-bromopenicillanate for the chloromethyl penicillanate 1,1-dioxide in the procedure of Example 2, the desired compound was obtained as an amorphous powder.

EXAMPLE 17

1,1-Dioxopenicillanoyloxymethyl 6-[(hexahydro-1(2H)-azocin-1-yl)-methyleneamino]-penicillanate hydrochloride By following the procedure described in Example 13 and substituting 6-[(hexahydro-1-(2H)-azocin-1-yl)-methyleneamino]-penicillanic acid for 6-[(hexahydro-1H-azepin-1-yl)-methyleneamino]penicillanic acid the title compound was obtained as a colourless freeze-dried powder.

The NMR-spectrum (CD$_3$OD, TMS as internal reference) showed peaks at δ=1.46 (s, 3H; 2-C$\underline{H}$$_3$), 1.57 (s, 6H; 2-C$\underline{H}$$_3$), 1.74 (s, 3H; 2-C$\underline{H}$$_3$), 1.5–2.0 (m, 10H; (C$\underline{H}$$_2$)$_5$), 3.2–3.8 (m, 6H; (C$\underline{H}$$_2$)$_2$N, 6α-$\underline{H}$ and 6β-$\underline{H}$), 4.48 (s, 1H; 3-$\underline{H}$), 4.63 (s, 1H; 3-$\underline{H}$), 4.93 (m, 1H, 5-$\underline{H}$), 5.53 (d, J=4 Hz, 1H; 6-$\underline{H}$), 5.63 (d, J=4 Hz, 1H, 5-$\underline{H}$), 5.97 (s, 2H; OC$\underline{H}$$_2$O), and 8.18 (s, 1H; N—C$\underline{H}$=N) ppm.

EXAMPLE 18

1-(1,1-Dioxopenicillanoyloxy)ethyl 6-[(hexahydro-1H-azepin-1-yl)-methyleneamino]-penicillanate hydrochloride To a solution of tetrabutylammonium 6-[(hexahydro-1H-azepin-1-yl)-methyleneamino]penicillanate (4.53 g, 8 mmol in ethyl acetate (40 ml), a solution of 1-iodoethyl 1,1-dioxopenicillanate (8.13 g, 38% pure, corresponding to 3.09 g, 8 mmol) in ethyl acetate (25 ml) was added. After stirring for 5 min. at ambient temperature, separated tetrabutylammonium iodide was filtered off and washed with ethyl acetate. From the filtrate the title compound was transferred to an aqueous phase (40 ml) with N hydrochloric acid (pH 3.0, 5° C.) and from the aqueous phase to an organic phase (ethyl acetate, 40 ml) with aqueous sodium hydrogen carbonate (pH 7.0, 5° C.). The organic phase was washed with water and the title compound was again transferred to an aqueous phase as described above. Freeze-drying of the aqueous phase gave the title compound as a colourless solid.

The NMR spectrum (D$_2$O) showed peaks at δ=1.50(s), 1.56(s), 1.61(s), 1.66(d,J=7), 1.73(s), 1.5–2.0(m), 3.20–3.85(m), 4.61(s), 4.75(s), 5.10(m), 5.53(d,J=4), 5.68(d,J=4), 7.05(q,J=7), and 8.03(s).

EXAMPLE 19

1,1-Dioxo-6-(2,6-dimethoxybenzamido)penicillanoyloxymethyl-6-[(hexahydro-1H-azepin-1-yl)-methyleneamino]penicillanate, hydrochloride Sodium 6-[(hexahydro-1-H-azepin-1-yl)-methyleneamino]penicillanate (0.7 g, 2 mmol) was added to an ice-cold solution of iodomethyl 1,1-dioxo-6-(2,6-dimethoxybenzamido)penicillanate (1.11 g, 2 mmol) in dimethylformamide (10 ml). After stirring for 30 minutes at room temperature the mixture was diluted with ethyl acetate (40 ml) and washed with water (4×10 ml).

The organic phase was stirred with water while hydrochloric acid was added to pH=3. The aqueous phase was freeze-dried to yield the title compound as a colourless powder.

The NMR-spectrum (CD$_3$OD), TMS as internal reference) showed signals at δ=1.47 (s, 3H; 2-C$\underline{H}$$_3$), 1.58 (s, 6H; 2-C$\underline{H}$$_3$), 1.76 (s, 3H; 2-C$\underline{H}$$_3$), 1.25–2.25 (m, 8H; (C$\underline{H}$$_2$)$_4$), 3.5–4.0 (m, 4H; (C$\underline{H}$$_2$)$_2$N), 3.83 (s, 6H; OC$\underline{H}$$_3$), 4.67 (s, 1H; 3-$\underline{H}$), 4.70 (s, 1H; 3-$\underline{H}$), 5.29 (d, J=4 Hz, 1H; 5-$\underline{H}$), 5.5–5.8 (m, 2H; 5-$\underline{H}$ and 6-$\underline{H}$), 6.03 (m, 2H; OC$\underline{H}$$_2$O), 6.26 (d, J=4 Hz, 1H; 6-$\underline{H}$), 6.71 (d, 2H; arom. 3-$\underline{H}$ and 5-$\underline{H}$), 7.41 (t, 1H; arom. 4-$\underline{H}$), and 8.21 (s, 1H, N—C$\underline{H}$=N) ppm.

EXAMPLE 20

Clavulanoyloxymethyl 6-[(hexahydro-1H-azepin-1-yl)-methyleneamino]-penicillanate Lithium clavulanate (0.1 g, 0.5 mmol) was added to a solution of iodomethyl 6-[(hexahydro-1H-azepin-1-yl)-methyleneamino]penicillanate (0.23 g, 0.5 mmol) in hexamethyl phosphoric acid triamide (3 ml). After stirring for 90 minutes at room temperature the mixture was diluted with ethyl acetate (20 ml) and washed with water (4×10 ml). The organic phase was stirred with water (20 ml) while hydrochloric acid was added to pH 3. The aqueous phase was separated and stirred with ethyl acetate (10 ml) while aqueous sodium bicarbonate was added to pH 7. The organic phase was dried and evaporated to leave an oil which was purified by chromatography on Sephadex LH-20 (8 g). The title compound was isolated as a colourless oil.

The NMR-spectrum (CDCl$_3$, TMS as internal reference) showed signals at δ=1.49(s, 3H; 2-C$\underline{H}$$_3$), 1.65(s, 3H; 2-C$\underline{H}$$_3$), 1.4–2.0 (m, 8H; (C$\underline{H}$$_2$)$_4$), 3.11(d, J=17 Hz, 1H; 6β-$\underline{H}$), 3.48(dd, J=17 Hz, J=3 Hz, 1H; 6α-$\underline{H}$), 3.3–3.6(m, 4H; (C$\underline{H}$$_2$)$_2$N), 4.22(d, J=7 Hz, 2H; C$\underline{H}$$_2$OH), 4.41(s, 1H, 3-$\underline{H}$), 4.91(t, J=7H, 1H, C=C$\underline{H}$), 5.08(s, 1H; 3-$\underline{H}$), 5.18(d, J=4 Hz, 1H; 6-$\underline{H}$), 5.51(d, J=4 Hz, 1H; 5-$\underline{H}$), 5.68(d, J=3 Hz, 1H; 5-$\underline{H}$), 5.87(m, 2H; O-C$\underline{H}$$_2$O), and 7.60(s, 1H; N-C$\underline{H}$=N) ppm.

EXAMPLE 21

6β-Bromopenicillanoyloxymethyl
6-[(hexahydro-1H-azepin-1-yl)-methyleneamino]-
penicillanate hydrochloride Potassium 6β-bromopenicillanate (535 mg, 1.68 mmol) was added to a solution of iodomethyl 6-[(hexahydro-1H-azepin-1-yl)-methyleneamino]penicillanate (6.52 mg, 1.40 mmol) in dimethylformamide (15 ml). After stirring for 30 minutes at room temperature, the mixture was diluted with ethyl acetate (60 ml) and washed with water (4×15 ml). The organic phase was separated and concentrated in vacuo to about 20 ml. To the concentrate was added water (15 ml), and the apparent pH of the stirred mixture was adjusted to 3 by addition of 0.5 N hydrochloric acid. The aqueous phase was separated and freeze-dried to yield the title compound as a colourless foam.

The NMR spectrum ($D_2O$) showed signals at $\delta = 1.48$ (s, 3H; 2-C$\underline{H}_3$), 1.51 (s, 3H; 2-C$\underline{H}_3$), 1.62 (s, 3H; 2-C$\underline{H}_3$), 1.68 (s, 3H; 2-C$\underline{H}_3$), 1.4–2.0 (m, 8H; (C$\underline{H}_2$)$_4$), 3.47–3.75 (m, 4H; (C$\underline{H}_2$)$_2$N), 4.71 (s, 1H; 3-$\underline{H}$), 4.76 (s, 1H; 3-$\underline{H}$), 5.46, 5.59, 5.62, and 5.66 (4d, J~4 Hz, 8H; 5-$\underline{H}$ and 6-$\underline{H}$), 5.93 (s, 2H; OC$\underline{H}_2$O), and 7.97 (s, 1H; N—C$\underline{H}$=N) ppm.

EXAMPLE 22

6β-Iodopenicillanoyloxymethyl
6-[(hexahydro-1H-azepin-1-yl)-methyleneamino]-
penicillanate hydrochloride Following the procedure described in Example 21, but substituting potassium 6β-iodopenicillanate for the corresponding 6β-bromopenicillanate, the title compound was obtained as a colourless powder.

The IR spectrum (KBr) showed strong bands at 1780 and 1680 cm$^{-1}$.

EXAMPLE 23

1,1-Dioxopenicillanoyloxymethyl
6-[(hexahydro-1H-azepin-1-yl)-methyleneamino]-
penicillanate hydrochloride

A. Tetrabutylammonium 6β-aminopenicillanate

To a stirred, ice-cooled mixture of 6β-aminopenicillanic acid (4.32 g, 20 mmol), tetrabutylammonium hydrogen sulphate (6.8 g, 20 mmol), dichloromethane (50 ml), and water (20 ml) was added slowly a solution of sodium hydroxide (1.60 g, 40 mmol) in water (3.5 ml). The organic layer was separated, and the aqueous layer was extracted with dichloromethane (2×25 ml). The combined organic layers were dried and evaporated in vacuo to leave the desired compound as a viscous oil.

The IR spectrum (CHCl$_3$) showed strong bands at 1760 and 1610 cm$^{-1}$.

B. 1,1-Dioxopenicillanoyloxymethyl 6β-aminopenicillanate hydrochloride

To a solution of tetrabutylammonium 6β-aminopenicillanate (5.1 g, 11 mmol) in ethyl acetate (25 ml) was added a solution of iodomethyl penicillanate, 1,1-dioxide (3.73 g, 10 mmol) in ethyl acetate (25 ml). After stirring for 15 min. at room temperature, the precipitate was filtered off, and the filtrate was evaporated in vacuo. The residue was purified by column chromatography on Sephadex ® LH 20 using chloroform-hexane 65:35 as eluent. The purified product was dissolved in ethyl acetate (25 ml), water (25 ml) was added, and the pH-value of the mixture was adjusted to 2.0 by addition of 2 N hydrochloric acid.

The aqueous phase was separated and freeze-dried to give the title compound as a colourless powder.

The NMR spectrum ($D_2O$) showed signals at $\delta = 1.52$ (s, 3H; 2-C$\underline{H}_3$), 1.60 (s, 3H; 2-C$\underline{H}_3$), 1.65 (s, 3H; 2-C$\underline{H}_3$), 1.76 (s, 3H; 2-C$\underline{H}_3$), 3.52–3.8 (s, 2H; 6-$\underline{H}$), 4.78 (s, 1H; 3-$\underline{H}$), 4.90 (s, 1H; 3-$\underline{H}$), 5.05–5.25 (m, 1H; 5-$\underline{H}$), 5.20 (d, J=4 Hz, 1H; 6-$\underline{H}$), 5.78 (d, J=4 Hz, 1H; 5-$\underline{H}$), and 6.08 (bs, 2H; OC$\underline{H}_2$O) ppm. TMS was used as external reference.

C. 1,1-Dioxopenicillanoyloxymethyl 6β-aminopenicillanate

The hydrochloride obtained according to Example 23 B was dissolved in water and cooled in an ice-bath. Ethyl acetate was added, and saturated aqueous sodium hydrogen carbonate was added while stirring until the pH in the aqueous phase was about 7. The organic phase was separated, dried, and evaporated in vacuo leaving the desired compound as a yellow oil.

D. 1,1-Dioxopenicillanoyloxymethyl 6-[(hexahydro-1H-azepin-1-yl)-methyleneamino]-penicillanate hydrochloride To an ice-cold solution of 1,-thioformyl-hexamethyleneimine (1.43 g) in dry dichloromethane (20 ml), triethyloxonium tetrafluoroborate (1.90 g) was added. The solution was stirred for half an hour at room temperature and again cooled in an ice-bath. An ice-cold solution of 1,1-dioxopenicillanoyloxymethyl 6β-aminopenicillanate (4.15 g) and N,N-diisopropylethylamine (1.80 ml) in dry dichloromethane (20 ml) was added, and the reaction mixture was slowly concentrated in vacuo at about 0° C. After about 3 hours, all solvent was evaporated off. The residue was extracted with diethyl ether (3×100 ml), and the diethyl ether extract was dried and treated with charcoal. Water (100 ml) was added, the apparent pH-value was adjusted to 2.5 by addition of 2 N hydrochloric acid, and the aqueous phase was freeze-dried to give the desired compound as an amorphous powder. It was identical with the compound described in Example 1.

EXAMPLE 24

1,1-Dioxopenicillanoyloxymethyl
6-[(hexahydro-1H-azepin-1-yl)-methyleneamino]-
penicillanate hydrochloride To a solution of 1,1-dioxopenicillanoyloxymethyl 6β-aminopenicillanate (4.15 g) and triethylamine (3.2 ml) in dry, alcohol-free chloroform (25 ml), 1-chloromethylenehexamethyleneiminium chloride (2.0 g) in dry, alcohol-free chloroform (10 ml) was added dropwise at a temperature of about −20° C. After standing for half an hour at −20° C., the temperature was raised to 0° C. within 15 minutes. The solution was evaporated in vacuo. The residue was stirred with diethyl ether (150 ml), and undissolved triethylamine hydrochloride was filtered off. Water (50 ml) was added, and the apparent pH-value of the mixture was adjusted to 2.5 by addition of 2 N hydrochloric acid. The aqueous phase was separated and freeze-dried to give the desired compound as an amorphous powder. It was identical with the compound described in Example 1.

What we claim is:
1. A compound of formula I

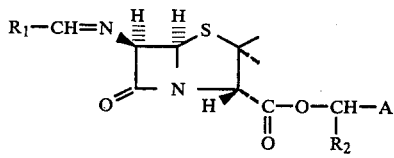

in which $R_1$ stands for a five- to ten-membered azacycloalkyl or azabicycloalkyl residue attached via the nitrogen atom and optionally being substituted by one or two, the same or different, lower alkyl groups; $R_2$ represents a hydrogen atom or a lower alkyl, phenyl or phenylalkyl radical; A represents a radical selected from the group consisting of (a) a radical of the formula II:

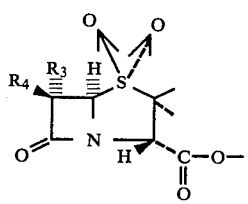

in which $R_3$ stands for a hydrogen or a halogen atom; $R_4$ is a hydrogen atom or an amino or acylamino group, and where at least one of $R_3$ and $R_4$ is hydrogen;

(b) a radical of the formula III:

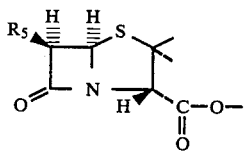

in which $R_5$ stands for a halogen atom; and (c) a radical of the formula IV:

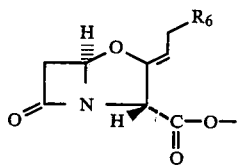

in which $R_6$ stands for a hydroxyl group or formula IV represents one of the radicals of known clavulanic acid derivatives with β-lactamase inhibitory activity;

and salts thereof with pharmaceutically acceptable, non-toxic acids.

2. A compound of formula I and according to claim 1, in which A stands for a radical of the formula II, $R_3$ and $R_4$ both representing a hydrogen atom; and pharmaceutically-acceptable, nontoxic salts thereof as defined in claim 1.

3. A compound of formula I and according to claim 1, in which A stands for a radical of the formula III, $R_5$ representing a halogen atom; and pharmaceutically-acceptable, nontoxic salts thereof as defined in claim 1.

4. A compound according to claim 1, in which $R_5$ stands for bromine or iodine.

5. A compound of formula I and according to claim 1, in which A stands for a radical of formula IV, $R_6$ representing a hydroxy group; and pharmaceutically-acceptable, nontoxic salts thereof as defined in claim 1.

6. A compound according to claim 1, in which $R_1$ represents piperidyl-1, hexahydro-1H-azepin-1-yl, hexahydro-1(2H)-azocin-1-yl, octahydro-1H-azonin-1-yl, 2-methyl-hexahydro-1H-azepin-1-yl, 3-methyl-hexahydro-1H-azepin-1-yl, 4-methyl-hexahydro-1H-azepin-1-yl, 2,6-dimethylpiperidyl-1, cis-3-azabicyclo[3.3.0]octyl-3, or cis-8-azabicyclo[4.3.0]-nonyl-8.

7. A compound according to claim 6, in which $R_1$ represents hexahydro-1H-azepin-1-yl, and $R_2$ represents hydrogen.

8. 1,1-Dioxopenicillanoyloxymethyl 6-[(hexahydro-1H-azepin-1-yl)-methyleneamino]penicillanate, and pharmaceutically-acceptable, nontoxic salts thereof with pharmaceutically acceptable, non-toxic acids.

9. 1,1-Dioxopenicillanoyloxymethyl 6-[(hexahydro-1(2H)-azocin-1-yl)-methyleneamino]penicillanate, and pharmaceutically-acceptable, nontoxic salts thereof with pharmaceutically acceptable, non-toxic acids.

10. 1,1-Dioxo-6-(2,6-dimethoxybenzamido)-penicillanoyloxymethyl 6-[(hexahydro-1H-azepin-1-yl)-methyleneamino]penicillanate, and pharmaceutically-acceptable, nontoxic salts thereof with pharmaceutically acceptable, non-toxic acids.

11. Clavulanoyloxymethyl 6-[(hexahydro-1H-azepin-1-yl)-methyleneamino]penicillanate, and pharmaceutically-acceptable, nontoxic salts thereof with pharmaceutically acceptable, non-toxic acids.

12. 1-(1,1-Dioxopenicillanoyloxy)ethyl 6-[(hexahydro-1H-azepin-1-yl)-methyleneamino]penicillanate, and pharmaceutically-acceptable, nontoxic salts thereof with pharmaceutically acceptable, non-toxic acids.

13. 6β-Bromopenicillanoyloxymethyl 6-[(hexahydro-1H-azepin-1-yl)-methyleneamino]penicillanate, and pharmaceutically-acceptable, nontoxic salts thereof with pharmaceutically acceptable, non-toxic acids.

14. 6β-Iodopenicillanoyloxymethyl 6-[(hexahydro-1H-azepin-1-yl)-methyleneamino]penicillanate, and pharmaceutically-acceptable, nontoxic salts thereof with pharmaceutically acceptable, non-toxic acids.

15. An antibacterial pharmaceutical preparation in dosage unit form for enteral, parenteral or topical treatment of patients (including animals) suffering from infectious diseases, which comprises as an active ingredient 0.025 g to 2.5 g of a compound as claimed in claim 1 together with an atoxic pharmaceutically acceptable carrier.

16. An antibacterial pharmaceutical preparation in dosage unit form as claimed in claim 15 for oral treatment of patients, containing from 0.05 g to 1.5 g of the active ingredient.

17. An antibacterial pharmaceutical preparation in dosage unit form as claimed in claim 15 and containing as the active component the compound 1,1-dioxopenicillanoyloxymethyl 6-[(hexahydro-1H-azepin-1-yl)-methyleneamino]penicillanate or a pharmaceutically-acceptable, nontoxic salt thereof with a pharmaceutically acceptable, non-toxic acid.

18. An antibacterial pharmaceutical preparation in dosage unit form as claimed in claim 15 and containing as the active component the compound 1,1-Dioxopenicillanoyloxymethyl 6-[(hexahydro-1-(2H)-azocin-1-yl)-methyleneamino]penicillanate or a pharmaceutically-acceptable, nontoxic salt thereof with a pharmaceutically acceptable, non-toxic acid.

19. An antibacterial pharmaceutical preparation in dosage unit form as claimed in claim 15 and containing as the active component the compound 1,1-dioxo-6-(2,6-dimethoxybenzamido)-penicillanoyloxymethyl 6-[(hexahydro-1H-azepin-1-yl)-methyleneamino]-penicillanate or a pharmaceutically-acceptable, nontoxic salt thereof with a pharmaceutically acceptable, non-toxic acid.

20. An antibacterial pharmaceutical preparation in dosage unit form as claimed in claim 15 and containing as the active component the compound clavulanoyloxymethyl 6-[(hexahydro-1H-azepin-1-yl)-methyleneamino]penicillanate or a pharmaceutically-acceptable, nontoxic salt thereof with a pharmaceutically acceptable, non-toxic acid.

21. An antibacterial pharmaceutical preparation in dosage unit form as claimed in any one of claims 17, 18, 19 or 20 in the form of tablets, pills, or capsules.

22. An antibacterial pharmaceutical composition containing a compound as claimed in claim 1 together with carrier substances and auxiliary agents, containing from 1% to 95% of the active compound.

23. An antibacterial compounded pharmaceutical composition as claimed in claim 22 containing the active ingredient together with a known penicillin, the ratio between the active compounds being between 1:20 and 20:1, preferably between 1:5 and 5:1.

24. An antibacterial compounded pharmaceutical composition as claimed in claim 23, in which the active ingredient is 1,1-dioxopenicillanoyloxymethyl 6-[(hexahydro-1H-azepin-1-yl)-methyleneamino]penicillanate, optionally being used in the form of a pharmaceutically-acceptable, nontoxic salt with a pharmaceutically acceptable, non-toxic acid, and the penicillin is 6-[D-$\alpha$-amino-$\alpha$-(p-hydroxyphenyl)acetamido]penicillanic acid.

25. In the treatment of patients suffering from infectious diseases, the administration of a compound as claimed in claim 1 in an amount of 3–200 mg/kg body weight of the patient/day, or an equivalent amount of a pharmaceutically-acceptable, nontoxic salt, as defined in claim 1, of a compound of formula I.

* * * * *